United States Patent [19]

Jackson et al.

[11] 4,252,951

[45] Feb. 24, 1981

[54] ISOLATION OF SYN-7-(2-AMINO-4-THIAZOLYL)-(METHOXYIMINO)ACETAMIDO-3-ACETOXYMETHYL-3-CEPHEM-4-CARBOXYLIC ACID

[75] Inventors: Billy G. Jackson; Donna A. Nezich, both of Indianapolis, Ind.

[73] Assignee: Eli Lilly and Company, Indianapolis, Ind.

[21] Appl. No.: 82,822

[22] Filed: Oct. 9, 1979

[51] Int. Cl.³ .................................... C07D 501/12
[52] U.S. Cl. .................................... 544/20; 544/28
[58] Field of Search .................................... 544/20, 28

[56] References Cited

U.S. PATENT DOCUMENTS

| | | | |
|---|---|---|---|
| 3,925,372 | 12/1975 | Chauvette | 424/246 |
| 4,098,888 | 7/1978 | Ochiai et al. | 424/246 |
| 4,152,432 | 5/1979 | Heymes et al. | 424/246 |
| 4,166,115 | 8/1979 | Takaya et al. | 424/246 |

FOREIGN PATENT DOCUMENTS 2348218  11/1977  France .

*Primary Examiner*—Paul M. Coughlan, Jr.
*Attorney, Agent, or Firm*—Joseph A. Jones; Arthur R. Whale

[57] ABSTRACT

Syn-7-(2-amino-4-thiazolyl)-(methoxyimino)-acetamido-3-acetoxymethyl-3-cephem-4-carboxylic acid is isolated by formation of cyclic ether solvates.

14 Claims, No Drawings

ISOLATION OF SYN-7-(2-AMINO-4-THIAZOLYL)-(METHOXYIMINO)ACETAMIDO-3-ACETOXYMETHYL-3-CEPHEM-4-CARBOXYLIC ACID

BACKGROUND

1. Field of the Invention

This invention provides a convenient process for isolating syn-7-(2-amino-4-thiazolyl) (methoxyimino) acetamido-3-acetoxymethyl-3-cephem-4-carboxylic acid by formation of crystalline cyclic ether solvates.

Prior Art

U.S. Pat. No. 4,152,432, of Roussel Uclaf, discloses syn-7-(2-amino-4-thiazolyl) (methoxyimino) acetamido-3-acetoxymethyl-3-cephem-4-carboxylic acid, an antibiotic cephalosporin hereinafter called compound A. The compound is an important member of a class of (2-amino-4-thiazolyl) (methoxyimino) cephalosporin compounds which have appeared in the literature before, and are now established as an important group of antibiotics.

The Roussel patent shows formic acid and ethanol solvates of syn-7-(2-amino-4-thiazolyl) (methoxyimino)acetamido-3-acetoxymethyl-3-cephem-4-carboxylic acid, which solvates are used in the crystallization of the compounds.

Solvates of cephalosporin antibiotics have frequently been observed and noted in the literature. For example, U.S. Pat. No. 3,925,372, of Chauvette, shows the preparation of a dimethylformamide solvate of 7-(D-phenylglycylamido)-3-chloro-3-cephem-4-carboxylic acid.

Solvates, however, are notoriously unpredictable substances. One can not predict what cephalosporin compounds will form solvates, nor the solvents with which solvates may be formed. It is noticeable that various salts, esters, and amino-protected derivatives of compound A have often been treated with cyclic ethers in the literature, but no prior worker has observed the solvates which have now been discovered to be formed with the unprotected acid form of the compound. See, for example, U.S. Pat. Nos. 4,152,432 and 4,098,888, and South African Pat. No. 77/2030.

SUMMARY OF THE INVENTION

This invention provides a process for isolating compound A from an aqueous reaction mixture in which the concentration of compound A is from about 0.07 mole/liter to about 0.4 mole/liter, which comprises performing in either order the steps of (1) adding to the aqueous reaction mixture an amount of a cyclic ether solvent chosen from tetrahydrofuran, 1,4-dioxane, 1,3-dioxolane or tetrahydropyran from about 0.1 volume of the aqueous reaction mixture to about 2 volumes of the aqueous reaction mixture, and (2) adjusting the pH of the mixture to a value from about 2.2 to about 3.2, and then allowing the mixture to stand until a precipitate of the solvate of compound A forms, and separating the precipitate.

DESCRIPTION OF THE PREFERRED EMBODIMENTS

The solvates of compound A which are disclosed here are useful in the method of isolating compound A which is provided by this invention.

It is difficult to isolate compound A in the free acid form from an aqueous reaction mixture. This difficulty is important since a highly preferred method of synthesizing the compound is carried out in an aqueous medium. See the U.S. Patent Application of George W. Huffman, filed on the same day with this document. The ease with which the solvates of this invention are precipitated from aqueous reaction mixtures accordingly makes possible the isolation process of this invention.

The aqueous reaction mixtures referred to herein are mixtures in which compound A has been synthesized. Usually the final step of the synthesis is the acylation step, in which the (2-amino-4-thiazolyl)-(methoxyimino)acetamido side chain is attached to the cephalosporin nucleus. Acylations of this type are preferably carried out in reaction mixtures in which the solvent is water or an aqueous water-miscible organic solvent, particularly aqueous acetone.

When the reaction solvent in the final step of the synthesis is an aqueous organic solvent, it is necessary to evaporate away a substantial amount of the organic solvent before compound A is isolated. Thus, the mixture in which the solvates are formed is herein referred to as an "aqueous reaction mixture." It is not necessary, of course, to remove every trace of organic solvent before adding the cyclic ether which forms the solvate. The exact amount of organic solvent which can be left in the aqueous reaction mixture depends upon the temperature, the concentration of compound A in the aqueous reaction mixture, and the amount of the cyclic ether which one is willing to use. In general, however, the amount of organic solvent should be reduced to below about 1–10 percent by volume before the solvate-forming solvent is added.

The concentration of compound A in the aqueous reaction mixture should be from about 0.07 mole/liter to about 0.4 mole/liter. However, the concentration of compound A must be adjusted for optimum yield in the synthesis process in which it is formed, and so it is not normally possible to adjust the concentration exclusively for the most efficient operation of the isolation process. It is preferred, however, to prepare the solvates from an aqueous reaction mixture wherein the concentration of compound A is from about 0.1 mole/liter to about 0.25 mole/liter.

The temperature at which the solvates are formed will usually be near the ambient temperature of the location of the process. That is to say, it will usually be in the range from about 15° C. to about 35° C. The temperature is not critical to the isolation process; the solvate can be formed and precipitated at temperatures from about 0° C. to about 40° C. When a lower temperature is used, the solvate can be expected to precipitate out more quickly and completely, but associated impurities may also precipitate out in greater quantity. Thus, the temperature of operation is chosen for the best convenience in the individual process concerned.

The precipitation of the compound A solvate is accomplished by adding the cyclic ether solvent to the aqueous reaction mixture, and adjusting its pH to a value from about 2.2 to about 3.2. These two steps may be performed in either order. It is preferable to add the solvent first.

The amount of the solvent to be added may be varied over wide limits. Amounts from about one-tenth of the volume of the aqueous reaction mixture, to about twice the volume, are useful; amounts from about 0.25 of the volume to about 0.7 of the volume are preferred. The amount of solvent to be used depends in part upon the concentration of compound A in the aqueous reaction mixture, because enough solvent must obviously be used to form the solvate. It would be most uneconomical, although possible, to use less solvent than is necessary to form a solvate with all of the compound A present. Depending upon the nature of the impurities in the aqueous reaction mixture, excess amounts of solvent, above the amount necessary to form the solvate, may be helpful to keep impurities in solution while the solvate is precipitated out.

The pH of the mixture is adjusted to from about 2.2 to about 3.2, and preferably to from about 2.2 to about 3.0, most preferably to about pH 2.7. Addition of an acid is necessary to obtain a pH in the desired range. The choice of the acid is not critical. It is most convenient to use a strong, inexpensive mineral acid such as hydrochloric acid or sulfuric acid. There is no objection, however, to using any reasonably strong acid which will not react with compound A or the solvate-forming solvent. For example, phosphoric acid, methanesulfonic acid, toluenesulfonic acid, or trifluoroacetic acid may be used if convenient in a given instance.

The solvent-containing mixture is then allowed to stand, with or without stirring, until a precipitate of the solvate of compound A is formed. Most conveniently, the mixture is simply allowed to stand without stirring at ambient temperature, as defined above. There is no objection to cooling the mixture to, for example, about 0° C., and it is also possible to isolate the solvate if the mixture is warmed, even to about 40° C. However, the precipitation of impurities at low temperatures may overbalance the speed of precipitation of the solvate at those temperatures. Of course, operation at elevated temperatures is likely to be uneconomical, because of increased solubility of the solvate at such temperatures. It is therefore usually uneconomical to operate the process at temperatures other than in the ambient temperature range.

When the precipitation of the solvate of compound A has proceeded to the desired extent, the solvate is separated by filtration, centrifugation or any other convenient means. The mixture is allowed to stand for a relatively brief period of time from a few minutes to about 24 hours, depending upon the concentration of compound A in the original aqueous reaction mixture, the temperature, and the nature of associated impurities. The optimum period to allow for precipitation is easily determined in any given case and depends upon the relative importance to the operator of obtaining complete precipitation, as against short batch time; a typical period is from 30 minutes to 2 hours.

The solvate may be used in the solvate form as an intermediate for processing, as for making salts of compound A which are to be used as antibiotics. Salt, especially the sodium salt, are the usual pharmaceutical form. The solvate may also be exhaustively dried, as under vacuum at moderately elevated temperatures in the range of from about 40° C. to about 60° C., to obtain compound A in the free acid form, usually containing some amount of residual solvate-forming solvent.

The following examples illustrate the isolation process of this invention. The solvates were identified by 60-megahertz nuclear magnetic resonance analysis (nmr) in DMSOd$_6$.

The products of the examples below were dried under vacuum at 40° C. for 16 hours before analysis.

The first group of examples illustrate variations of the preferred methods of carrying out the isolation of this invention.

EXAMPLE 1

A 45.5 g. portion of 7-aminocephalosporanic acid, p-toluenesulfonate salt, was added to 400 ml. of acetone and 400 ml. of water, and 85 ml. of 45% tripotassium phosphate solution was added to adjust the pH to 7.5. The mixture was stirred for 30 minutes, and 39.7 g. of a mixture of syn-(2-amino-4-thiazolyl)-(methoxyimino)acetic acid, 1H-benzotriazol-1-yl ester, and syn-1-[(2-amino-4-thiazolyl) (methoxyimino)acetyl]-3-hydroxy-1H-benzotriazolium, hydroxide inner salt, was added. The reaction mixture was then stirred for 4 hours, while the pH was maintained at 7.5 by the occasional addition of tripotassium phosphate solution.

The acetone was then removed from the mixture by evaporation under vacuum, and the pH was adjusted to 4.0 with about 50 ml. of 6 N hydrochloric acid. Two hundred ml. of tetrahydrofuran was added, the mixture was stirred for 5 minutes, and the pH was then adjusted to 2.8 with additional hydrochloric acid. The acid mixture was then stirred at ambient temperature for 90 minutes, and was filtered. The solids were washed with water, and dried to obtain 26.0 g. of the tetrahydrofuran solvate of compound A, containing 0.6 mole of tetrahydrofuran per mole of compound A.

Compound A was identified by nmr, which showed the following characteristic features:

δ 9.83 (d, 8 Hz, H), 7.32 (broad s, 2H), 6.81 (s, H), 5.87 (dd, 8 Hz+5 Hz, H), 5.20(d, 5 Hz, H), 4.92(q, 14 Hz+9 Hz, 2H), 3.90(s, 3H), 3.60(s, 2H), 2.07(s, 3H).

The presence and amount of tetrahydrofuran were indicated by its characteristic features in the nmr spectrum at δ 1.7–1.9(m).

EXAMPLE 2

Compound A was prepared as described in Example 1, except that the starting compound was 77.8 g. of acetone-wet 7-aminocephalosporanic acid, containing 35% of the pure compound. The solvate was formed and isolated as described in Example 1, except that the reaction mixture was allowed to stir at ambient temperature for one hour and 40 minutes after the pH was reduced to 2.7 in the final step of the process. The solids were dried to obtain 26.8 g. of the solvate, containing 0.5 mole of tetrahydrofuran per mole of compound A, as measured by nmr analysis.

The above solvate was then recrystallized by dissolving it in 600 ml. of water and 200 ml. of tetrahydrofuran by the addition of about 45 ml. of 45% aqueous tripotassium phosphate solution. The neutral solution was filtered on a filter-aid pad, and the pH was then lowered to 2.7 by the addition of hydrochloric acid. An additional 100 ml. of tetrahydrofuran was added, and the mixture was stirred at ambient temperature for 15 minutes and then in an ice-water bath for 15 minutes, and was left in the refrigerator overnight. The mixture was filtered and the solids were dried to obtain 20.0 g. of the tetrahydrofuran solvate of compound A.

EXAMPLE 3

Compound A was prepared as described in Example 2, and its tetrahydrofuran solvate was prepared and isolated as described in Example 2, except that after the pH was adjusted to 2.6 in the final step, the mixture was stirred at ambient temperature for 30 minutes, and then in a ice-water bath for 70 minutes. The mixture was then filtered cold, and the solids were dried to obtain 29.6 g. of the tetrahydrofuran solvate of compound A, containing 0.5 mole of tetrahydrofuran per mole of compound A.

The above product was recrystallized by dissolving it in water-THF as described in the recrystallization step of Example 2. The resulting solution was stirred for 30 minutes, its pH was adjusted to 2.8 with normal hydrochloric acid, and it was stirred for 30 minutes at ambient temperature and 60 minutes in an ice-water bath. The mixture was filtered and the solids were dried to obtain 24.7 g. of the tetrahydrofuran solvate of compound A, containing 0.5 mole of tetrahydrofuran per mole of compound A.

The group of examples which follow show additional methods of performing the isolation of this invention.

EXAMPLE 4

Compound A was synthesized as described in Example 2, except that the reaction mixture was stirred at ambient temperature for 2.5 hours, and then held overnight in a refrigerator, after addition of the mixed acylating agents. Acetone was then removed by evaporation under vacuum, and the pH of the aqueous reaction mixture was adjusted to 4.0 by addition of 6 N hydrochloric acid. The mixture was then extracted three times with 220-ml. portions of ethyl acetate. The water phase left after extraction was then adjusted to pH 2.6 with additional hydrochloric acid, and 100 ml. of tetrahydrofuran was added. Three hundred ml. of water and 100 ml. of additional tetrahydrofuran were added, and stirred while the precipitate of solvate formed. The mixture was then filtered and the solids were washed with acetone to obtain 21.5 g. of the tetrahydrofuran solvate of compound A, containing 0.3 mole of tetrahydrofuran per mole of compound A.

The following example shows that the presence of other organic solvents does not interfere with the present isolation step.

EXAMPLE 5

Compound A was synthesized as described in Example 4. Acetone was then evaporated, and the pH was adjusted to 4.0 as described in Example 4. A 250 ml. portion of 1:1 ethyl acetate:tetrahydrofuran was added, and stirred for a few minutes. The organic phase was separated, and a heavy white precipitate separated from the aqueous phase. The extraction was repeated four times, but no additional precipitation occurred. The precipitate was separated by filtration, and dried to obtain 18.2 g. of the tetrahydrofuran solvate of compound A, containing 0.4 mole of tetrahydrofuran per mole of compound A.

The following example illustrates the use of a solvate of this invention as a starting compound for preparing salts of compound A.

EXAMPLE 6

A 14.5 g. portion of the tetrahydrofuran solvate of compound A, prepared in Example 5, was suspended in 80 ml. of water and cooled in an ice bath. The pH was adjusted to 6.0 by the addition of 2 N sodium hydroxide solution, and the mixture was decolorized by adding charcoal and filtering through a talc pad. The mixture was then lyophilized to obtain 12.6 g. of compound A, sodium salt, containing 6.62% water.

EXAMPLE 7

A 37.8 g. portion of acetone-wet 7-aminocephalosporanic acid, 36% pure, was stirred with 200 ml. of water and 200 ml. of acetone, and the pH was adjusted to 7.5 by the addition of 45% aqueous tripotassium phosphate solution. Then 19.6 g. of syn-1-[(2-amino-4-thiazolyl)(methoxyimino)acetyl]-3-hydroxy-1H-benzotriazolium, hydroxide inner salt, was added in one portion, and the mixture was stirred at ambient temperature for four hours while the pH was maintained in the range 7.3-7.5. The acetone was then removed by evaporation under vacuum, and the pH was adjusted to 4.0 by the addition of about 20 ml. of 6 N hydrochloric acid. The mixture was filtered.

To 118 ml. of the filtrate was added 40 ml. of tetrahydrofuran, and the pH was then adjusted to 2.6 with additional hydrochloric acid. The mixture was stirred for 5 minutes at ambient temperature, then held for 16 hours in the refrigerator. The mixture was stirred for 5 minutes in an ice-water bath, and filtered. The solids were washed with a small amount of water and dried. The yield was 6.44 g. of the tetrahydrofuran solvate of compound A, containing about one mole of 1-hydroxybenzotriazole and about 0.4 mole of tetrahydrofuran per mole of compound A.

To an equal portion of the aqueous reaction mixture above was added 40 ml. of 1,4-dioxane, and the mixture was treated as described in the paragraph above. The solids were found to be 6.22 g. of the solvate of compound A, as indicated by nmr analysis, containing about 0.7 mole of 1,4-dioxane per mole of compound A. The presence and quantity of solvent were indicated by its characteristic feature in the nmr spectrum at $\delta$ 3.55(s). The solvate also contained about 2 moles of 1-hydroxybenzotriazole per mole of compound A.

EXAMPLE 8

Compound A was synthesized as described in Example 7. The volume of the aqueous reaction mixture after adjusting the pH to 4.0 was 355 ml. To one half of the aqueous reaction mixture was added 59 ml. of 1,3-dioxolane, the pH was adjusted to 2.6, and the resulting mixture was held overnight in the refrigerator. The mixture was then filtered, and the solids were rinsed with water and vacuum dried at 40° C. to obtain 10.5 g. of the solvate of compound A, containing 0.8 mole of 1,3-dioxolane per mole of compound A by nmr analysis, which showed the characteristics of 1,3-dioxolane at $\delta$ 3.75(s) and 4.77(s).

EXAMPLE 9

Compound A was synthesized as described in Example 8 above. The volume of the aqueous reaction mixture was 360 ml. after the pH was adjusted to 4.0, which volume was divided into two equal portions.

To one portion was added 60 ml. of tetrahydrofuran, and the pH of the mixture was adjusted to 2.6 by the addition of about 10 ml. of 6 N hydrochloric acid. The slurry was stirred for 30 minutes at ambient temperature, and it was then filtered. The solids were rinsed with water and dried to obtain 3.41 g. of the tetrahydrofuran solvate of compound A, containing 0.3 mole of tetrahydrofuran per mole of compound A by nmr analysis. Analysis by vapor-phase chromatography indicated 5.1% of tetrahydrofuran, equivalent to 0.34 mole of tetrahydrofuran per mole of compound A.

To the other portion of the aqueous reaction mixture was added 60 ml. of 1,4-dioxane, and the mixture was then treated as described in the paragraph above to obtain 1.94 g. of the solvate of compound A, containing 0.3 mole of 1,4-dioxane per mole of compound A according to nmr analysis. Analysis by vapor-phase chromatography indicated 3.5% of 1,4-dioxane, equivalent to 0.18 mole of 1,4-dioxane per mole of compound A.

EXAMPLE 10

The process of Example 9 was repeated, except for the solvents used for the formation of the solvates.

To one half of the 350 ml. of aqueous reaction mixture was added 57 ml. of 1,3-dioxolane, and the pH was adjusted to 2.6 with 6 N hydrochloric acid. The mixture was stirred for 30 minutes and filtered. The solids were washed with water and vacuum dried for 16 hours at 45° C. to obtain 3.22 g. of the 1,3-dioxolane solvate of compound A. Nmr analysis indicated that the solvate contained 0.4 mole of 1,3-dioxolane per mole of compound A. Vapor-phase chromatography analysis of the solvate indicated 4.8% of 1,3-dioxolane, equivalent to 0.30 mole of 1,3-dioxolane per mole of compound A.

To the other half of the aqueous reaction mixture was added 25 ml. of tetrahydropyran, and the pH was adjusted to 2.6 as usual. The mixture was then stirred for 30 minutes at ambient temperature, and filtered. The solids were rinsed with water and vacuum dried for 16 hours at 45° C. to obtain 8.77 g. of the tetrahydropyran solvate of compound A, which was shown by nmr analysis to contain some 1-hydroxybenzotriazole. Nmr analysis of the solvate indicated 0.6 mole of tetrahydropyran per mole of compound A; the characteristic nmr feature of tetrahydropyran was seen at δ 1.5–1.7(m). Vapor-phase chromatography analysis indicated 5.9% of tetrahydropyran, equivalent to 0.32 mole of tetrahydropyran per mole of compound A.

We claim:

1. A process for isolating syn-7-(2-amino-4-thiazolyl) (methoxyimino)acetamido-3-acetoxymethyl-3-cephem-4-carboxylic acid from an aqueous reaction mixture in which the concentration of the cephem is from about 0.07 mole per liter to about 0.4 mole per liter, which process comprises performing in either order the steps of (1) adding to the aqueous reaction mixture an amount of a cyclic ether solvent chosen from tetrahydrofuran, 1,4-dioxane, 1,3-dioxolane or tetrahydropyran from about 0.1 volume of the aqueous reaction mixture to about 2 volumes of the aqueous reaction mixture, and (2) adjusting the pH of the mixture to a value from about 2.2 to about 3.2, and then allowing the mixture to stand until a precipitate of the solvate of syn-7-(2-amino-4-thiazolyl) (methoxyimino)acetamido-3-acetoxymethyl-3-cephem-4-carboxylic acid forms, and separating the precipitate.

2. A process of claim 1 wherein the concentration of syn-7-(2-amino-4-thiazolyl) (methoxyimino)acetamido-3-acetoxymethyl-3-cephem-4-carboxylic acid in the aqueous reaction mixture is from about 0.1 mole per liter to about 0.25 mole per liter.

3. A process of claim 1 wherein the solvent is added before the pH adjustment.

4. A process of claim 1 wherein the amount of tetrahydrofuran, 1,4-dioxane, 1,3-dioxolane or tetrahydropyran is from about 0.25 volume of the aqueous reaction mixture to about 0.7 volume of the aqueous reaction mixture.

5. A process of claim 1 wherein the pH is adjusted to from about 2.2 to about 3.0.

6. A process of claim 1 wherein the temperature of the process is from about 15° C. to about 35° C.

7. A process of either claim 1,2,3,4,5 or 6 wherein tetrahydrofuran is added.

8. A process of claim 2 wherein the pH is adjusted to from about 2.2 to about 3.0.

9. A process of claim 8 wherein the amount of tetrahydrofuran, 1,4-dioxane, 1,3-dioxolane or tetrahydropyran is from about 0.25 volume of the aqueous reaction mixture to about 0.7 volume of the aqueous reaction mixture.

10. A process of claim 9 wherein the temperature of the process is from about 15° C. to about 35° C.

11. A process of claim 10 wherein the concentration of syn-7-(2-amino-4-thiazolyl) (methoxyimino)acetamido-3-acetoxymethyl-3-cephem-4-carboxylic acid in the aqueous reaction mixture is from about 0.1 mole per liter to about 0.25 mole per liter.

12. A process of claim 11 wherein the solvent is added before the pH adjustment.

13. A process of claim 12 wherein tetrahydrofuran is added.

14. A process of either claim 8,9,10 or 11 wherein tetrahydrofuran is added.

* * * * *